United States Patent
Petrick et al.

(10) Patent No.: US 7,120,230 B2
(45) Date of Patent: Oct. 10, 2006

(54) SYSTEM AND METHOD FOR ELIMINATING THE EFFECTS OF SATURATED PIXELS IN SOLID STATE X-RAY DETECTORS

(75) Inventors: Scott William Petrick, Sussex, WI (US); Douglas Albagli, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 95 days.

(21) Appl. No.: 10/838,429

(22) Filed: May 3, 2004

(65) Prior Publication Data

US 2005/0243968 A1    Nov. 3, 2005

(51) Int. Cl.
*H05G 1/30* (2006.01)

(52) U.S. Cl. ..................... 378/98.8; 378/116

(58) Field of Classification Search ............... 378/98.8, 378/116, 19, 62, 98.11, 98.12, 94, 97; 250/370.09
See application file for complete search history.

(56) References Cited

U.S. PATENT DOCUMENTS 6,106,152 A * 8/2000 Thunberg .................... 378/205
6,904,124 B1 * 6/2005 Staver et al. .................. 378/62
2002/0070365 A1 * 6/2002 Karellas ....................... 250/581
2003/0030004 A1 * 2/2003 Dixon et al. ............ 250/370.09
2005/0207533 A1 * 9/2005 Nagai ......................... 378/98.8

* cited by examiner

Primary Examiner—Edward J. Glick
Assistant Examiner—Hoon Song
(74) Attorney, Agent, or Firm—McAndrews, Held & Malloy, Ltd.; Peter J. Vogel; Michael A. Dellapenna

(57) ABSTRACT

A system and method for collecting x-ray exposure data in an x-ray detector include scanning pixels in an x-ray detector to determine exposure levels. The scanning may progress sequentially from a first edge to an opposite edge or may progress in an alternating fashion across the detector. The detector may include a data line split, where an object may be positioned between the data line split and an x-ray source. The scanning may then progress sequentially from at least one detector edge towards the data line split. In addition, a system for collecting x-ray exposure data in an x-ray detector is described. The system includes a detector, a plurality of data lines and scan lines, and a programmable logic device. The programmable logic device communicates at least one of a scan line driver module direction signal, an enable scan line driver module signal, and a cascade signal.

8 Claims, 5 Drawing Sheets

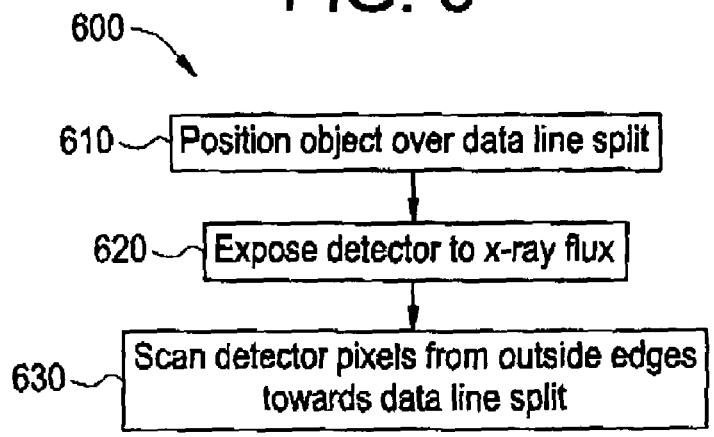
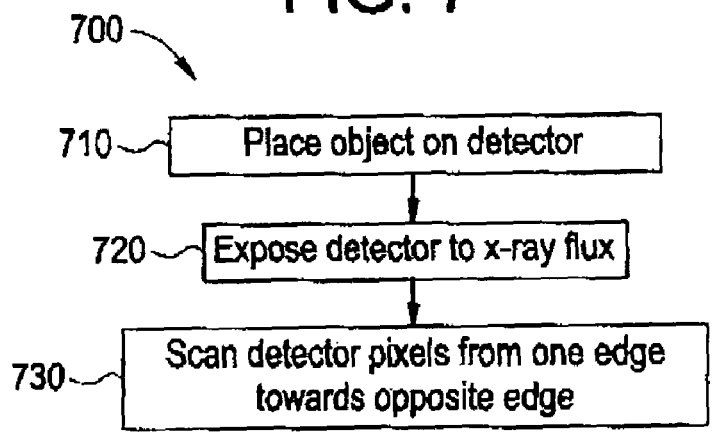
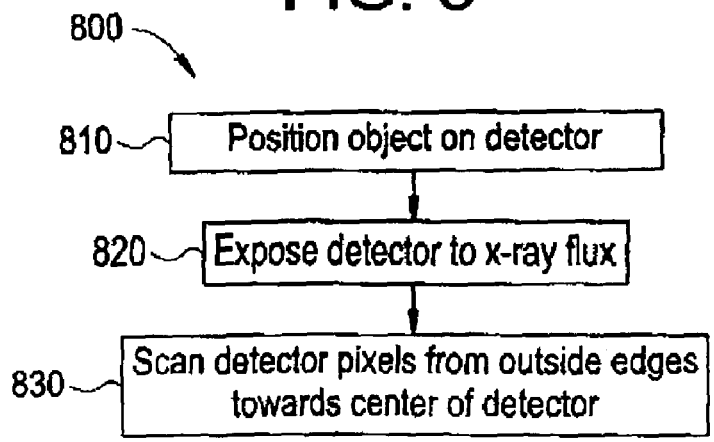

SYSTEM AND METHOD FOR ELIMINATING THE EFFECTS OF SATURATED PIXELS IN SOLID STATE X-RAY DETECTORS

BACKGROUND OF THE INVENTION

The present invention relates generally to medical diagnostic imaging systems, and in particular relates to a system and method for the elimination of the effects of saturated pixels in solid state x-ray detector images.

X-ray imaging has long been an accepted medical diagnostic tool. X-ray imaging systems are commonly used to capture, as examples, thoracic, cervical, spinal, cranial and abdominal images that often include information necessary for a physician to make an accurate diagnosis. X-ray imaging systems typically include an x-ray source and an x-ray detector. When having a thoracic x-ray image taken, for example, a patient stands with his or her chest against the x-ray sensor as an x-ray technologist positions the x-ray detector and the x-ray source at an appropriate height. X-rays produced by the source travel through the patient's chest, and the x-ray detector then detects the x-ray energy generated by the source and attenuated to various degrees by different parts of the body. An associated control system obtains the detected x-ray energy from the x-ray detector and prepares a corresponding diagnostic image on a display.

In addition, x-ray images may be used for many other purposes. For instance, internal defects in a target object may be detected by x-ray images. Additionally, changes in internal structure or alignment of a target object may be determined from an examination of an x-ray image. Furthermore, the x-ray image may show the presence or absence of objects in the target. The information gained from x-ray imaging has applications in many fields other than medicine, including, for example, manufacturing.

The x-ray detector may be a conventional screen/film configuration, in which the screen converts the x-rays to light that exposes the film. The x-ray detector may also be a solid state digital image detector. Digital detectors afford a significantly greater dynamic range than conventional screen/film configurations.

FIG. 1 illustrates an exemplary solid state x-ray detector 100. The solid state x-ray detector 100 includes an array of picture elements (pixels 150), an x-ray conversion layer 120 and readout electronics 140.

The array of pixels includes a plurality of pixels 150. Each pixel 150 includes a switching element ("switch") and a light detector. Typically, the pixel 150 switch is a field effect transistor ("FET") and the light detector is a photodiode. The pixels 150 are generally composed of amorphous silicon. The x-ray conversion layer 120 may be a layer of CsI deposited on the pixel array.

The array of pixels 150 may be arranged in columns 170 and rows 160. Generally, the pixels 150 included in a row 160 are connected to a data line via the pixel 150 switch. A data line may be a conductor common to all pixels 150 in a given row 160. Each data line is connected to readout electronics 140. The readout electronics 140 measure the amount of charging current supplied to pixels 150 connected to a data line.

Generally, the pixels 150 included in a column 170 are connected to a scan line via control terminals of the pixel 150 switches. The scan line may be common to all pixels 150 in a given column 170. A scan line may be asserted to allow charging current to flow from the readout electronics 140 to the pixels 150 connected to the scan line. The various scan lines may be connected to scan drivers. The scan drivers may be included in a data acquisition system 190. The scan drivers activate a given scan line by asserting the scan line.

Prior to x-ray exposure, the detector 100 must be initialized. Initialization of the detector 100 occurs by charging each photodiode in the various pixels 150 with a reverse bias voltage to a known voltage. This is naturally accomplished in the course of scanning the detector 100. The readout electronics 140 provide a constant voltage on each of the data lines. As the data acquisition system 190 asserts each scan line (via a scan driver, as described above), the FET in each pixel 150 connected to that scan line conducts electrical charge from the data line connected to that pixel 150. In this way, the photodiode for each pixel 150 of the scan line may be recharged to the potential difference between the data line and a common electrode. Since the common electrode generally has a negative potential with respect to the data line, the photodiode is generally reversed biased, and therefore does not conduct charge other than leakage current. Therefore, the photodiode may then simply store the charge provided via the data line.

In operation, the photodiodes in the pixels 150 measure an amount of x-ray exposure. When incident x-ray flux strikes the x-ray conversion layer 120, the layer 120 converts the x-ray flux into light. The amount of light converted by the layer 120 is generally proportional to the intensity of the incident x-ray flux. The light then strikes the photodiodes in the pixels 150. Each photodiode is initially charged with a known amount of reverse bias voltage. When the light strikes the photodiodes, the photodiodes conduct and an amount of electric charge is discharged from the initially charged amount of reverse bias voltage in the photodiode. That is, the incident light discharges some or all of the reverse bias voltage initially charged in the photodiodes. The amount of discharged voltage in the photodiodes is generally proportional to the intensity of incident light, which is generally proportional to the intensity of the incident x-ray flux. Therefore, the amount of discharged voltage in photodiodes is generally proportional to the intensity of incident x-rays.

After the conclusion of the exposure, the voltage on the photodiode is restored to the initial voltage. The amount of charge required to restore the photodiode to the initial voltage is measured as restoring charge. The restoring charge is therefore a measurement of the x-ray flux intensity integrated by the pixel 150 during the length of the exposure.

The detector 100 is scanned by the readout electronics 140 in a manner similar to the structure of the pixel array. The detector 100 is scanned on a column-by-column basis for the various columns 170 of pixels 150 in the pixel array. In operation, a scan line is asserted by a scan driver in the data acquisition system 190. As described above, each of the pixels 150 along the scan line is connected to a separate data line. When the scan line is asserted, the gates of the FETs in the pixels 150 connected to the scan line conduct. The data line then conducts the charge to the photodiode that has been discharged due to x-ray exposure. As each scan line is asserted in turn, the initial voltage is restored to all of the photodiodes of the pixels 150 in the scan line simultaneously by the readout electronics 140 over the individual data lines. The amount of restoring charge for each pixel 150 is provided by the readout electronics 140 through the data lines.

The scan drivers may assert the individual scan lines in a given sequence. Therefore, the pixel 150 array may be read-out, or scanned, by selectively asserting a scan line, followed by asserting a different scan line, and so on, until all of the desired pixels 150 have been read-out by asserting the associated scan lines.

In any imaging system, x-ray or otherwise, image quality is important. X-ray imaging systems utilizing digital or solid state image detectors ("digital x-ray systems") experience certain electrical phenomena that may cause imaging difficulties. Imaging difficulties may be caused by effects such as electronic current leakage from imaging system circuitry, x-ray detectors, and the like.

At least one region of interest ("ROI") may be identified in an exposure of the detector 100. Generally, the ROI is an area of the detector 100 where the object being examined impedes the path of incident x-rays to the detector 100. The ROI is an area of the detector 100 where the detector 100 may receive a lesser intensity of x-ray flux intensity. Therefore, as described above, less incident x-ray flux may be converted into light by the scintillator 120, causing less voltage to be discharged in the various photodiodes of the pixels 150. Pixels 150 located within the ROI are therefore unsaturated pixels 150.

Pixels 150 located outside the ROI may be exposed to raw x-ray beams and therefore may become completely discharged of the initial voltage. Pixels 150 that become completely discharged of the initial voltage are saturated pixels 150. Saturated pixels 150 place a large amount of electronic stress on the photodiode FETs. In addition, for detectors 100 that use a scintillator and a photodiode, optical light emitted from the scintillator may be absorbed in the active area (particularly the FETs) causing an increase in this leakage current.

Because the exact location of the various saturated pixels 150 may be unknown prior to the scanning of the detector 100, each saturated pixel 150 on a data line may add an indeterminable amount of leakage current to the signal of each pixel 150 scanned prior to the saturated pixel 150 in the data line. If the saturated pixels 150 on a data line are scanned after unsaturated pixels 150 in the ROI on the same data line, the leakage current from the saturated pixels 150 may add to and corrupt the signal obtained from the unsaturated pixels 150. The reading of an unsaturated pixel 150 before a saturated pixel 150 in a data line therefore may cause the signal read from the unsaturated pixel 150 to become corrupted.

When the signal read from the unsaturated pixel 150 becomes corrupted, the x-ray intensity experienced by the unsaturated pixel 150 is inaccurate in the resultant x-ray image. For example, an unsaturated pixel 150 with a corrupted signal (caused by the reading of the unsaturated pixel 150 before a saturated pixel 150) may appear to have been exposed to a greater x-ray intensity than the actual x-ray intensity exposed to the unsaturated pixel 150. This, in turn causes the unsaturated pixel 150 to appear lighter in the resultant x-ray image. In addition, leakage current from the saturated pixels 150 may cause edges of an object to become blurred in the resultant x-ray image. As such, leakage current from the saturated pixels 150 may cause degradation in x-ray image accuracy, contrast and quality.

Many solid state x-ray detectors currently use a "split data line" design. FIG. 2 illustrates an exemplary split data line detector 200. The split line detector 200 includes several data lines 210, a data line split 230 and several scan lines 250. As described above, each data line 210 includes a plurality of pixels 150. Each data line 210 does not extend across the full vertical length of the detector 200. The various data lines 210 extend from opposite edges of the detector 200 to the center of the detector 200. The data lines 210 in the two halves of the detector 200 meet at a data line split 230. The scan lines 250 also include a plurality of pixels 150. Each scan line 250 extends across the full length of the detector 200.

In operation, an object is placed above the detector 200 and is exposed to x-ray flux. As described above, pixels 150 in the detector 200 located underneath the object are located in an ROI 220. The pixels 150 in the ROI 220 are generally unsaturated pixels 240. Pixels 150 outside of the ROI 220 receive raw x-ray beams and are therefore generally saturated pixels 260. In this way, a pixel 150 may be either an unsaturated pixel 240 or a saturated pixel 260, depending on the amount of stored charge that is discharged in the pixel 150.

When the split data line detector 200 is scanned, a scan line 250 along the top of the detector 200 and a scan line 250 across the bottom of the detector 200 are activated simultaneously. The simultaneous activation of the scan lines 250 causes all the pixels 150 along those two respective scan lines 250 in the top and the bottom of the detector 200 to be read simultaneously. After the top and bottom rows of pixels 150 are read, the respective scan lines 250 are deactivated, and the second-to-top scan line 250 and the second-to-bottom scan line 250 are activated. The sequential activation, scanning and deactivation of adjacent scan lines 250 continues from the scan lines 250 at the opposite edges of the detector 200 and ends at the data line split 230.

However, as described above, leakage current from saturated pixels 260 read after unsaturated pixels 240 may corrupt the resultant signal. According to the direction of the progression of scan line 250 activation, scanning and deactivation illustrated in FIG. 2, the split data line detector 200 reads many saturated pixels 260 after the unsaturated pixels 240 of the ROI 220. Thus, the signal from many of the unsaturated pixels 240 of the ROI 220 may become corrupted from the leakage current of the saturated pixels 260.

Therefore, a need exists for a method and system for reading the signals from a solid state x-ray detector to reduce the effects of saturated pixels on the signals from unsaturated pixels.

BRIEF SUMMARY OF THE INVENTION

The present invention provides a system and method for eliminating effects of saturated pixels in solid state x-ray detectors. The system includes an x-ray detector comprising first and second pixels, an x-ray flux source and readout electronics. The method includes providing an x-ray detector comprising first and second pixels, exposing the detector and pixels to an x-ray flux, and scanning the first pixel before the second pixel. During exposure, the first and second pixels are exposed to first and second x-ray intensities, with the first x-ray intensity being greater than the second x-ray intensity. The scanning includes measuring the x-ray intensities for both the first and second pixels.

The x-ray flux source exposes the detector and pixels to an x-ray flux. The first and second pixels are exposed to first and second x-ray intensities, respectively. The first x-ray intensity is greater than the second x-ray intensity. The readout electronics scan the first pixel in order to measure the first x-ray intensity before scanning the second pixel in order to measure the second x-ray intensity. The first and second pixels may be included in a first plurality of pixels extending linearly from a first detector edge towards an opposite detector edge. The first pixel may also be closer to the first detector edge than the second pixel.

In addition, the system may further include a data line split and a second plurality of pixels. The second plurality of pixels may extend linearly from the opposite detector edge to the data line split. The first plurality of pixels then also extend linearly from the first detector edge towards the data line split. The system may also include an anatomy being examined, where the anatomy is placed between the detector and the x-ray source. The anatomy may be located between the data line split and the x-ray source. Furthermore, the data line split may be located at a center of the detector.

The readout electronics of the system may scan the first plurality of pixels by progressively scanning from a pixel at the first detector edge to a first pixel at the data line split. The readout electronic may also similarly scan the second plurality of pixels by scanning from a pixel at the opposite detector edge towards a second pixel at the data line split.

The first plurality of pixels may alternatively extend continuously from the first detector edge to the opposite detector edge. The readout electronics may scan the first plurality of pixels by progressing sequentially from a pixel at the first detector edge towards a pixel at the opposite detector edge. The system may also include an anatomy being examined, where the anatomy is located between the opposite detector edge and the x-ray source.

The readout electronics may instead scan the continuous first plurality of pixels in an alternating progression, where the alternating progression proceeds by scanning a pixel at the first detector edge, followed by a pixel at the opposite detector edge, followed by a pixel adjacent to the pixel at the first detector edge, followed by a pixel adjacent to the pixel at the opposite detector edge, where the alternating progression continues to scan the first plurality of pixels by scanning pixels adjacent to previously scanned pixels.

In addition, a system for collecting x-ray exposure data in an x-ray detector is disclosed. The system includes an x-ray detector, a plurality of data line readout modules, a plurality of scan line driver modules, and a programmable logic device. The x-ray detector includes a plurality of data lines, a plurality of scan lines, and a plurality of pixels. Each of the data lines is connected to a row of the pixels, and each of the scan lines is connected to a column of pixels. The data lines are connected to the data line readout modules. The scan lines are connected to the scan line driver modules. The programmable logic device communicates with the scan line driver modules, where the communication includes at least one of a scan line driver module direction signal, an enable scan line driver module signal, and a cascade signal.

The scan line driver direction module direction signal may determine which scan line driver module is to be asserted next. The enable scan line driver module signal may cause at least one of the scan line driver modules to assert at least one of the scan lines. The cascade signal may indicate a deassertion of at least one of the scan lines by at least one of the scan line driver modules.

BRIEF DESCRIPTION OF SEVERAL VIEWS OF THE DRAWINGS

FIG. 6 depicts a flowchart for a method for the proper positioning of an object on a detector with a data line split and the scanning of the detector to eliminate effects of saturated pixels, used in accordance with an embodiment of the present invention.

FIG. 7 depicts a flowchart for a method for the scanning of a detector without a data line split to eliminate effects of saturated pixels used in accordance with an embodiment of the present invention.

FIG. 8 depicts a flowchart for a method for the scanning of a detector without a data line split mimicking the functionality of a detector with a data line split, used in accordance with an embodiment of the present invention.

DETAILED DESCRIPTION OF THE INVENTION

Figure 1:
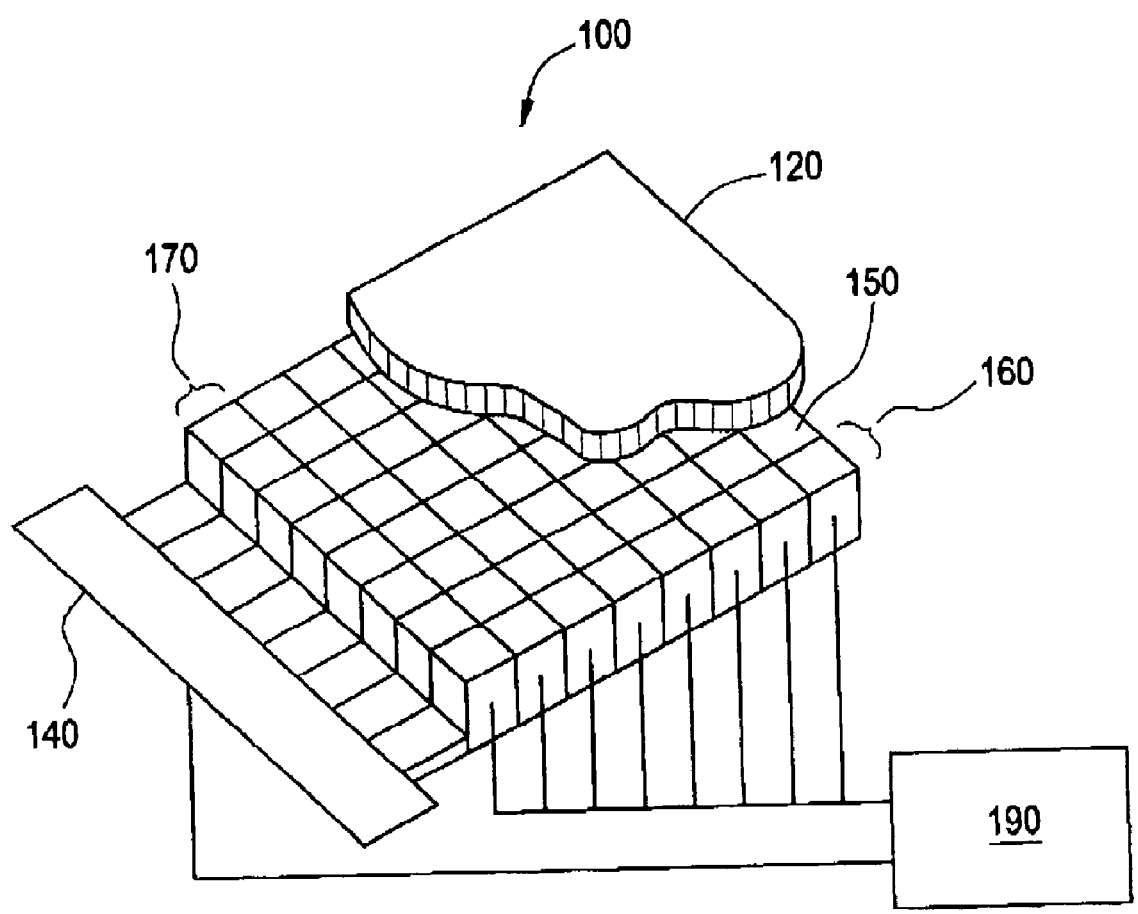
FIG. 1 depicts an exemplary solid state x-ray detector.
Figure 2:
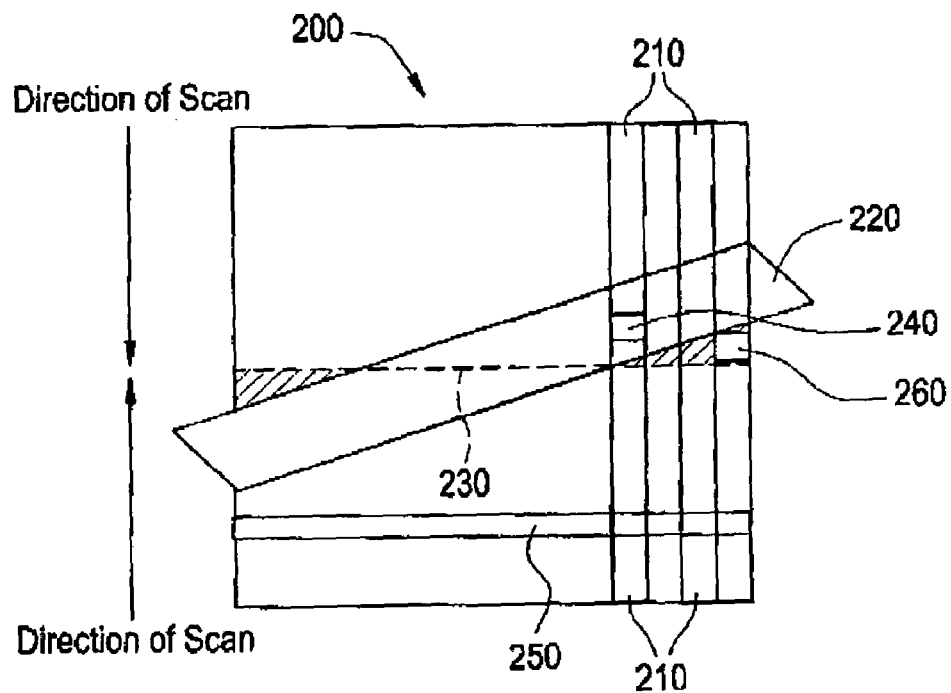
FIG. 2 depicts an exemplary split data line detector.
Figure 3:
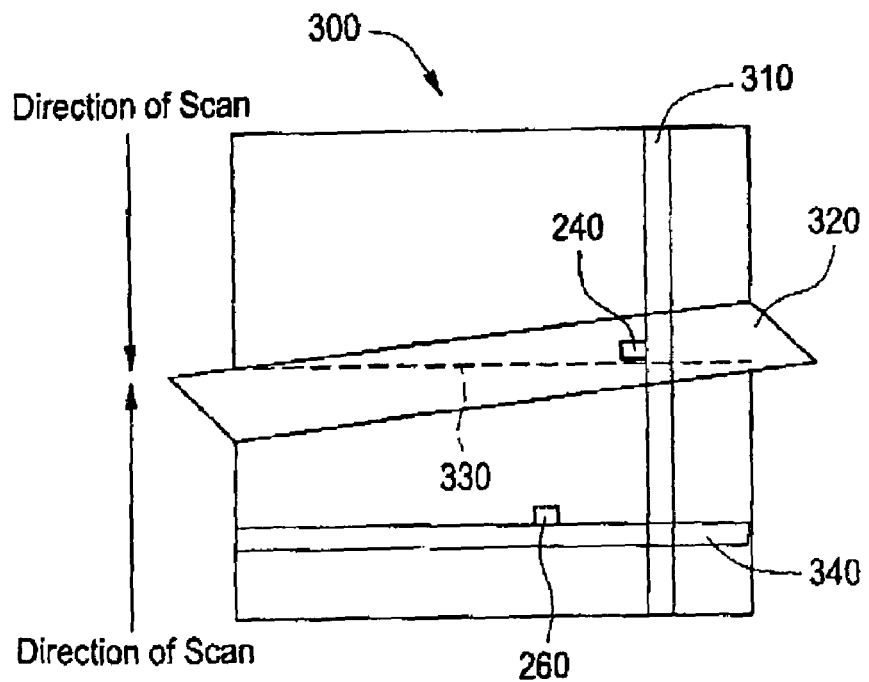
FIG. 3 depicts a split data line detector with proper object positioning used in accordance with an embodiment of the present invention.

FIG. 3 depicts a split data line detector 300 with proper object positioning used in accordance with an embodiment of the present invention. The detector 300 includes a plurality of data lines 310, a plurality of scan lines 340 and a data line split 330.

As described above, each data line 310 includes a plurality of pixels 150. Each data line 310 may not extend across the full vertical length of the detector 300. The various data lines 310 may extend from opposite edges of the detector 300 to the center of the detector 300. The data lines 310 therefore preferably extend from opposite edges of the detector 300 to a data line split 330 at the center of the detector 300. However, the data line split 330 need not be located at the center of the detector 300.

Each scan line 340 also includes a plurality of pixels 150. Each scan line 340 may extend across the full length of the detector 300. The data lines 310 and scan lines 340 interconnect an array of pixels 150 in the detector 300.

In operation, an object is positioned in relation to the detector 300 and is exposed to x-ray flux. As described above, pixels 150 in the detector 300 located in an area of the detector 300 corresponding to the object are located in an ROI 320. As described above, the pixels 150 located in the ROI 320 generally are unsaturated pixels 240. Pixels 150 outside of the ROI 320 may receive raw x-ray beams and are therefore generally saturated pixels 260. A pixel 150 may be either an unsaturated pixel 240 or a saturated pixel 260. In an embodiment, the ROI 320 may include an area less than the entire object being scanned.

The object is positioned in order to place the resultant ROI 320 over the data line split 330 relative to an x-ray source. The object is therefore positioned over the data line split 330 relative to an x-ray source. When the detector 300 is scanned by readout electronics 140 (as described above), a scan line 340 along the top of the detector 300 and a scan line 340 across the bottom of the detector 300, for example, are activated simultaneously. The simultaneous activation causes the pixels 150 in the respective scan lines 340 along the top and the bottom of the detector 300 to be read simultaneously. After the top and bottom rows of pixels 150 are read, scan lines 340 are deactivated, and the second-to-top scan line 340 and the second-to-bottom scan line 340 are activated. In continuing the progression, adjacent scan lines 340 are activated, scanned and deactivated, enabling the pixels in the split data line detector 310 to be scanned in rows simultaneously from the top scan line 340 to the data line split 330 and from the bottom scan line 340 to the data line split 330.

As described above, leakage current from saturated pixels 260 read after unsaturated pixels 240 may corrupt the resultant signal. However, by positioning the object to be examined over the data line split 330, the detector 300 tends to scan saturated pixels 260 before the unsaturated pixels 240 of the ROI 320. The detector 300 is scanned along each of the scan lines 340, starting from the top and bottom edges of the detector 300 (edges where the pixels 150 have been exposed to raw x-ray beams and therefore have become saturated) towards the data line split 330 surrounded by the ROI 320. Consequently, along each data line 310, the saturated pixels 260 tend to be scanned prior to the unsaturated pixels 240. Therefore, along each data line 310, the saturated pixels 260 are preferably read first and the saturated pixel 260 leakage current may be eliminated before the unsaturated pixels 240 in the ROI 320 are read.

In addition, an exact centering of the object or ROI 320 over the data line split 330 relative to an x-ray source is unnecessary. The object or ROI 320 may only be located over each half of the detector 300 for the length of the data line split 330. Therefore, all saturated pixels 260 may be read before the unsaturated pixels 240 located below the object and ROI 320 during the normal scanning progression.

Alternatively, the scanning progression may not scan every scan line 340 of the detector 300. Instead, the detector 300 may have scan lines 340 closer to the data line split 330 activated first, with the progression of scanning adjacent scan lines 340 towards the data line split 330 being the same as in the above embodiment of the present system. Therefore, the scanning of the detector 300 may begin at scan lines 340 other than those on the outer edges of the detector 300. This is advantageous in situations where an x-ray collimator is used to reduce the area of the detector 300 exposed to less than that of the entire detector 300, for example, resulting in fewer saturated pixels 260, particularly along the edges of the detector 300.

Figure 4:
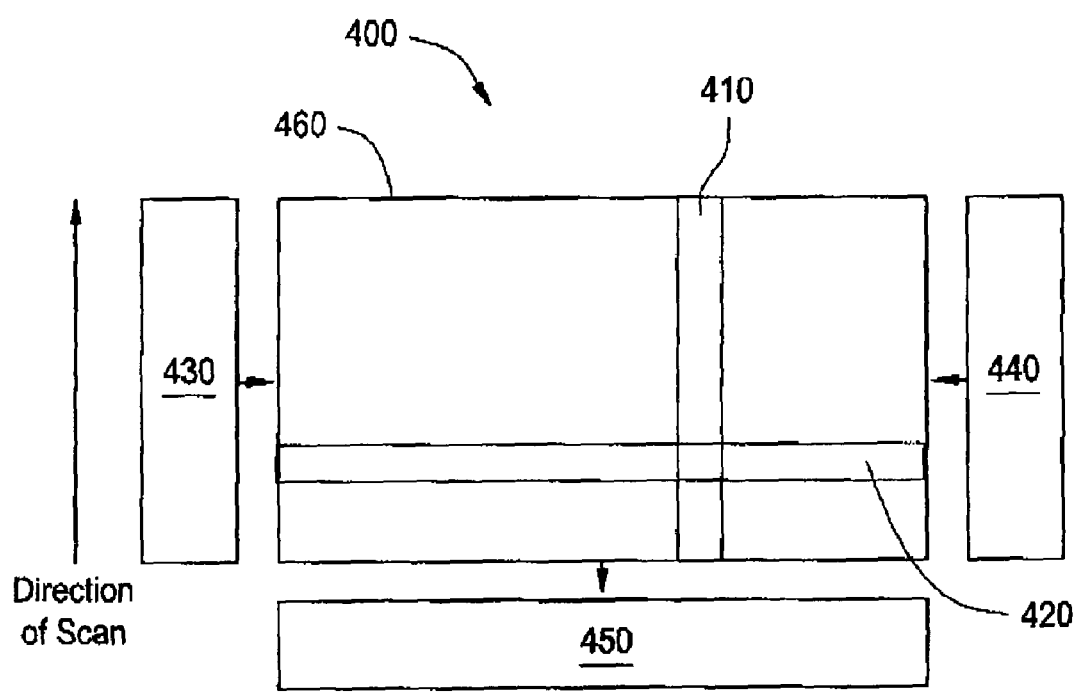
FIG. 4 depicts a detector without a data line split used in accordance with an embodiment of the present invention.

FIG. 4 depicts a detector 400 without a data line split used in accordance with an embodiment of the present invention. The detector 400 includes a plurality of data lines 410, a plurality of scan lines 420, an odd scan line driver module 430, an even scan line driver module 440, odd and even data line readout modules 450 and an anatomy wall 460. As described above, each data line 410 and scan line 420 interconnect a plurality of pixels 150. The odd and even data line readout modules 450 include an odd data line readout module and an even data line readout module.

The data lines 410 may be numbered sequentially starting from either the right or left side of the detector 400. The odd-numbered data lines 410 may be connected to the odd data line readout module 450 by a first set of interlaced electrical data line contacts. The even-numbered data lines 410 may be connected to the even data line readout module 450 by a second set of interlaced electrical data line contacts.

The scan lines 420 may be numbered sequentially starting from either the top or bottom of the detector 400. The odd-numbered scan lines 420 may be connected to the odd scan line driver module 430 by electrical contacts. The even-numbered scan lines 420 may be connected to the even scan line driver module 440 by electrical contacts.

In accordance with one embodiment of the present invention, the detector 400 may be used as a mammographic detector. In this embodiment, the anatomy wall 460 may placed against the chest of a patient, just below the patient's breast to be examined, for example. The design of the present detector 400 allows very small edge-of-detector active area to chest wall distance so as to provide good chest wall imaging coverage. By connecting the odd scan line driver module 430, the even scan line driver module 440 and the odd and even data line readout modules 450 to three edges of the detector 400, a fourth edge of the detector 400, namely the anatomy wall 460, is allowed to come as close as possible to the patient's chest wall.

In operation, the anatomy wall 460 may be placed against the patient's chest wall. The patient's breast and the detector 400 are then exposed to an x-ray flux. As described above, when a patient's breast is exposed to an x-ray flux, the pixels 150 located below the breast may be located within an ROI and may become unsaturated pixels 240. The pixels 150 located outside the ROI may receive raw x-ray beams and may therefore become saturated pixels 260.

The pixels 150 in the detector 400 may then be scanned by activating the scan line 420 on the detector 400 edge farthest from the anatomy wall 460. The scan line 420 may be an odd or even-numbered scan line 420, as described above, depending on how the scan lines 420 have been numbered.

If the scan line 420 along the edge of the detector 400 opposite the anatomy wall 460 is an odd-numbered scan line 420, then the scan line 420 may be activated by the odd scan line driver module 430. Conversely, if the scan line 420 along the edge of the detector 400 opposite the anatomy wall 460 is an even-numbered scan line 420, then the scan line 420 may be activated by the even scan line driver module 440.

As described above, each pixel 150 in the scan line 420 is attached to a different data line 410. The odd data line readout module of the odd and even data line readout modules 450 reads the pixels 150 associated with and connected to the odd-numbered data lines 410. The even data line readout module of the odd and even data line readout modules 450 reads the pixels 150 associated with and connected to the even-numbered data lines 410.

After the scan line 420 farthest from the object wall 460 is activated and the pixels 150 connected to the scan line 420 are read, the scan line 420 is deactivated. The next adjacent scan line 420 closer to the anatomy wall 460 may then be activated. If the scan line 420 farthest from the anatomy wall 460 was an odd-numbered scan line 420, then the next scan line 420 to be activated may be an even-numbered scan line 420 and may correspondingly be activated by the even scan line driver module 440. Conversely, if the scan line 420 farthest from the anatomy wall 460 was an even-numbered scan line 420, then the next scan line 420 to be activated may be an odd-numbered scan line 420 and may correspondingly be activated by the odd scan line driver module 430.

As described above, each pixel 150 in the scan line 420 is attached to a different data line 410. The odd data line readout module of the odd and even data line readout modules 450 reads the pixels 150 connected to the odd-numbered data lines 410. The even data line readout module of the odd and even data line readout modules 450 reads the pixels 150 connected to the even-numbered data lines 410. The progressive pixel 150 reading sequence may repeat until all even and odd scan lines 420 have been activated and all pixels 150 have been scanned.

The pixel 150 reading sequence may cause saturated pixels 260 to be scanned before unsaturated pixels 240. As described above, as the anatomy wall 460 may be closer to the ROI than the opposite edge of the detector 400 where the progressive pixel 150 reading sequence begins, by scanning the pixels 150 with data lines 410 from the edge opposite the anatomy wall 460 towards the anatomy wall 460, saturated pixels 260 may generally be read before the unsaturated pixels 240.

Figure 5:
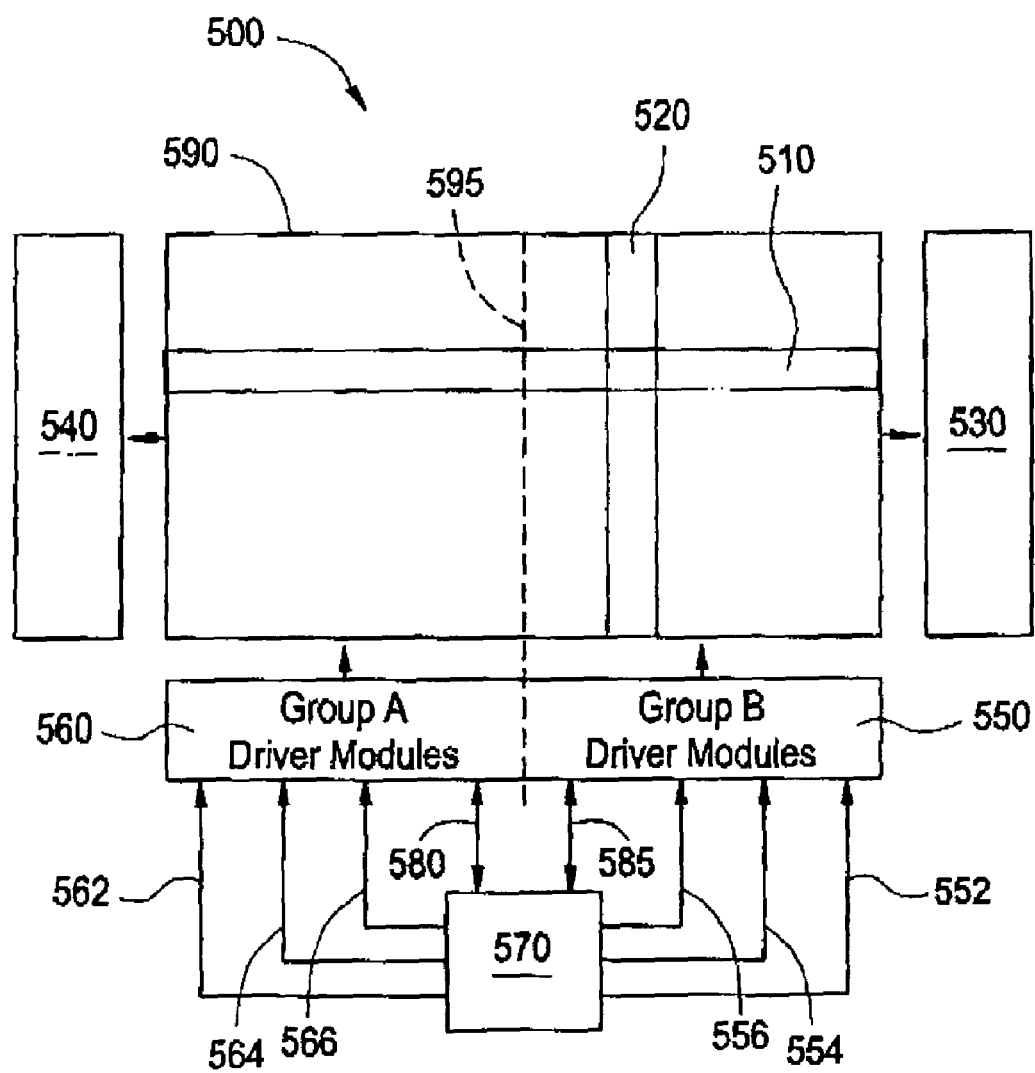
FIG. 5 depicts a detector without a data line split mimicking the functionality of a detector with a data line split, used in accordance with an embodiment of the present invention.

Alternatively, FIG. 5 depicts a detector 500 without a data line split mimicking the functionality of a detector with a data line split, used in accordance with an embodiment of the present invention. The detector 500 includes a plurality of data lines 510, a plurality of scan lines 520, an even data line readout module 530, an odd data line readout module 540, group A scan line driver modules 560, group B scan line driver modules 550, a programmable logic device ("PLD") 570 and an anatomy wall 590.

The group A scan line driver modules 560 may include at least one group A even scan line driver module and at least one group A odd scan line driver module. The group B scan line driver modules 550 may include at least one group B even scan line driver module and at least one group B odd scan line driver module.

The data lines 510 may extend from the left edge of the detector 500 to the right edge of the detector 500. An imaginary data line split 595 may serve as a line of reference dividing the surface area of the detector 500 in half, for example. In addition, the imaginary data line split 595 may serve as a line of reference for the center of the data lines 510. Therefore, the imaginary data line split 595 may act as a line of reference dividing both the detector 500 and data lines 510 in half, but the imaginary data line split 595 may not physically divide the detector 500 or the data lines 510. The imaginary data line split 595 primarily serves as a reference line for the pixel 150 scanning progression, as described below.

Similar to the detector 400 of FIG. 4, the data lines 510 of the detector 500 may be numbered sequentially starting from either the top or bottom edge of the detector 500. The odd-numbered data lines 510 may be electrically connected to the odd data line readout module 540. The even-numbered data lines 510 may be electrically connected to the even data line readout module 530.

The scan lines 520 may be numbered sequentially starting from either the left or right edge of the detector 500. The scan lines 520 on the right side of the imaginary data line split 595 may be electrically connected to the group B scan line driver modules 550. The scan lines 520 on the left side of the imaginary data line split 595 may be electrically connected to the group A scan line driver modules 560.

The odd-numbered scan lines 520 on the left side of the imaginary data line split 595 may be electrically connected to at least one group A odd scan line driver module of the group A scan line driver modules 560 by a set of interlaced electrical contacts. The even-numbered scan lines 520 on the left side of the imaginary data line split 595 may be electrically connected to at least one group A even scan line driver module of the group A scan line driver modules 560 by a set of interlaced electrical contacts.

The odd-numbered scan lines 520 on the right side of the imaginary data line split 595 may be electrically connected to the at least one group B odd scan line driver module of the group B scan line driver modules 550 by a set of interlaced electrical contacts. The even-numbered scan lines 520 on the left side of the imaginary data line split 595 may be electrically connected to the at least one group B even scan line driver module of the group B scan line driver modules 550 by a set of interlaced electrical contacts.

The PLD 570 may be any logic-driven device. For example, the PLD 570 may be a software application in a computer. The PLD 570 may also be an integrated circuit, an application-specific integrated circuit ("ASIC") or other software or hardware programmable logic device, for example.

The PLD 570 may be electrically connected to the group B scan line driver modules 550 and to the group A scan line driver modules 560. The PLD 570 may communicate various commands through electronic signals to the group B scan line driver modules 550 and to the group A scan line driver modules 560. In addition, the group B scan line driver modules 550 and/or the group A scan line driver modules 560 may send data to the PLD 570. The various signals sent between the group A scan line driver modules 560 and/or the PLD 570 may include a group A direction signal 562, a group A enable odd scan line driver module signal 564, a group A enable even scan line driver module signal 566 and a group A cascade signal 580, for example. The various signals sent between the group B scan line driver modules 550 and the PLD 570 may include a group B direction signal 552, a group B enable odd scan line driver module signal 554, a group B enable even scan line driver module signal 556 and a group B cascade signal 585, for example.

The group A direction signal 562 and/or the group B direction signal 552 may have a logic setting of either "HIGH" or "LOW," for example. Both direction signals 562 and 552 may control the order in which the various scan line driver modules progress, namely the group A scan driver modules 560 and the group B scan driver modules 550. Therefore, direction signals 562 and 552 control which output of the respective scan line driver module is to be activated next, and which scan line driver module follows when the last output of a scan line driver module has been activated. If both group A direction signal 562 and group B direction signal 552 have a logic setting of "HIGH," the scan line driver modules in group A 560 and group B 550 may progress in the same order, for example left to right. Conversely, if the group A direction signal 562 has a logic setting of "HIGH" and the group B direction signal 552 has a logic setting of "LOW," the scan line driver modules for group A 560 and group B 550 may progress in the opposite order, for example. For example, the group A scan line driver modules 560 progress left to right while the group B scan line driver modules 550 progress right to left.

The various enable signals, namely the group A enable odd scan line driver module signal 564, the group A enable even scan line driver module signal 566, the group B enable odd scan line driver module signal 554 and the group B enable even scan line driver module signal 556 may activate the scan driver modules, for example. The group A enable odd scan line driver module signal 564 may therefore activate the odd-numbered scan lines 520 on the left side of the detector 500 while the group A enable even scan line driver module signal 566 may activate the even-numbered scan lines 520 on the left side of the detector 500. Conversely, the group B enable odd scan line driver module signal 554 may activate the odd-numbered scan lines 520 on the right side of the detector 500 while the group B enable even scan line driver module signal 556 may activate the even-numbered scan lines 520 on the right side of the detector 500.

The cascade signals 580 and 585 may indicate the completion of scanning for the scan line driver modules 550, 560 on either side of the imaginary split 595. The individual scan line driver modules that are associated with the group A enable odd scan line module signals 564 connect logically from one odd-numbered module to the next in the group A scan line driver modules 560. The logical connection is performed via the PLD 570. For example, in the group A scan driver module 560, a group A cascade signal 580 with an indication or value of "start" may be communicated by the PLD 570 to the group A scan driver module 560. That is, a group A cascade signal 580 may be communicated between the group A scan driver module 560 and the PLD 570 indicating to "start" the scanning of the pixels 150 associated with given scan line 520. The group A and group B scan driver modules 560 and 550, respectively, may be further subdivided into even and odd scan driver modules. The cascade signals 580 and 585 may be faithful to this scheme as well. For example, odd cascade signals might go through the PLD 570, but only between odd scan driver modules in a group of scan driver modules if the detector is operated in an alternating, or "ping-pong" fashion. Alternatively, for example, the odd cascade signals might go through the PLD 570, including between group A and B scan driver modules 550, 560 if the detector is operated in a sequential or progressive fashion. The same scanning progression may apply to the even cascade signals. In this way, the even and odd scan driver modules in a given group are treated separately by the PLD 570.

Similarly, on the opposite side of the group A scan driver module 560, for example, a group A cascade signal 580 with an indication or value of "end" may be communicated by the group A scan driver module 560 to the PLD 570. Once the PLD 570 receives the group A cascade signal 580 with a value of "end," the PLD 570 may then communicate a group B cascade signal 585 with an indication or value of "start" to the group B scan line driver modules 550. This may be necessary for a scanning mode that is purely progressive, such as a mode that starts at an edge of the detector 500 and proceeds to scan each scan line 520, moving scan line 520 by scan line 520 towards the imaginary data line split 595, for example.

This same arrangement may also apply for the group A even scan line driver modules 560 and group B even scan line driver modules 550. The cascade signals 580 and 585 may be bi-directional, based on the state of the scan driver module's direction input. That is, for one state of the group A direction signal 562 in progressive mode, the group A cascade signal 580 would be communicated through the PLD 570 from the group A scan driver module 560 to the group B scan driver module 550, and from the group B scan driver module 550 to the group A scan driver module 560 for the opposite other state of the group A direction signal 562, for example. In a non-progressive, alternating scanning mode, for example, the communication of the group A cascade signal 580 flow may be interrupted by the PLD 570.

In one embodiment of the invention, the detector 500 may be positioned so the anatomy wall 590 is placed against a patient's chest. The detector 500 may be placed below the patient's breast. The detector 500 may then be exposed to an x-ray dose.

The detector 500 may be scanned in a reading progression so as to mimic the split data line detector 300 of FIG. 3. The pixel reading sequence of detector 500 may occur as follows, for example. First, the group A direction signal 562 and the group B direction signal 552 may be assigned complementary logic settings. For example, the group A direction signal 562 has a "HIGH" setting while the group B direction signal 552 has a "LOW" setting. After a scan line 520 on the left edge of the detector 500 is scanned, the next scan line 520 scanned may be on the right edge of the detector 500, for example. Conversely, after a scan line 520 in the right side of the detector 500 is scanned, the next scan line 520 scanned may be immediately to the right of the last scanned scan line 520 in the left side of the detector 500, for example. Similarly, the next scanned scan line 520 may be on the right side of the detector 500, immediately to the left of the last scanned scan line 520 on the right side of the detector 500.

The PLD 570 may activate a scan line 520 via the group A enable odd scan line driver module signal 564, group A enable even scan line driver module signal 566, group B enable odd scan line driver module signal 554 or group B enable even scan line driver module signal 556. For example, the PLD 570 may activate the first scan line 520 via the group A enable odd scan line driver module signal 564, assuming the left most scan line 520 is an odd scan line 520.

Next, the PLD 570 may activate the right-most scan line 520 via the group B enable even scan line driver module 556 if the right-most scan line 520 is an even scan line, or via the group B enable odd scan line driver module 554 if the right most scan line 520 is an odd scan line.

Next, the PLD 570 may activate the second scan line 520 via the group A enable even scan line driver module signal 566.

Next, the PLD 570 may activate the second scan line 520 from the right edge of the detector 500. If the second scan line 520 from the right edge of the detector 500 is an even scan line 520, the activation may occur via the group B enable even scan line driver module 556. If the second scan line 520 from the right edge of the detector 500 is an odd scan line 520, the activation may occur via the group B enable odd scan line driver module 554.

The PLD 570 may continue the activation of succeeding scan lines 520 in an alternating fashion, namely 1) group A enable odd scan line driver module 564, 2) group B enable even scan line driver module 554, 3) group A enable even scan line driver module 566, 4) group B enable odd scan line driver module 556, etc, for example. The alternating progression of scans continues until the scanning reaches the imaginary data line split 595.

The detector 500 may therefore be scanned in a fashion mimicking the split data line detector 300 of FIG. 3 even though the data lines 510 in the detector 500 of FIG. 5 are continuous across the entire detector 500. As the patient's breast is generally located over the center of the detector 500 where the imaginary data line split 595 is located, for example, the ROI and corresponding unsaturated pixels 150 are also located over the imaginary data line split 595. Therefore, the alternating progression of scanning the data lines 510 of the detector 500 ensures the scanning of saturated pixels 150 outside the ROI before the unsaturated pixels 150 within the ROI.

Alternatively, because all of the cascade signals 580 and 585 are provided to the PLD 570, the PLD 570 may be programmed to interrupt the progression of scanning. The PLD 570 may be configured to stop the progression of scans once the PLD 570 receives a cascade signal 580 or 585 from any given scan line drive module 550 or 560. Therefore, the PLD 570 may be programmed to scan a limited portion of the detector 500, starting at either edge of the detector 500.

Alternatively, the PLD 570 may be configured to start scanning at a scan line 520 other than the scan line 520 on the edge of the detector 500. The PLD 570 may be programmed to scan only in a limited number of scan lines 520 around the imaginary data line split 595.

Alternatively, the PLD 570 may be configured to skip the scanning of various scan lines 520. For example, the PLD 570 may be programmed to scan only the scan lines 520 numbered 100 through 1200 on the left side of the detector 500. Therefore, the PLD 570 scans scan line 520 numbered 100, then scans scan line 520 numbered 101, then scans scan line 520 numbered 102, and so on, until scan line 520 numbered 1200 is reached and scanning stops, for example. Therefore, the detector 500 may be limited to the scanning of scan lines 520 in an ROI on one side of the detector 500 or one area on one side of the detector 500, for example.

FIG. 6 depicts a flowchart for a method 600 for the proper positioning of an object on a detector with a data line split and scanning of the detector to eliminate effects of saturated pixels, used in accordance with an embodiment of the present invention. First, at step 610, the object to be examined may be placed in relation to a detector having a data line split. The object may be positioned so the object covers the data line split. The object need not be perfectly centered over the data line split as long as at least a portion of the object is located over each half of the detector for the length of the data line split.

Next, at step 620, the detector may be exposed to an x-ray flux. The x-ray flux may cause pixels in the detector to discharge stored electrical charge, as described above. Furthermore, pixels covered by the object may discharge less electrical charge, and may therefore become unsaturated pixels. However, pixels outside the object may discharge most, if not all, of their stored electrical charge and may therefore become saturated pixels.

Finally, at step 630, the pixels in the detector may be scanned along the scan lines associated with the various pixels from the outside edges of the detector towards the data line split. The outer scan lines on the edges parallel to the data line split may be activated, scanned for data, then deactivated first. Next, the scan lines adjacent to the outer scan lines may be activated, scanned and deactivated. Next, the scan lines third from the outer edges may be scanned. The progression may continue until all the scan lines in the detector have been scanned and the data line split has been reached.

Alternatively, at step 630, the scanning may begin with scan lines other than the scan lines on the outer edges of the detector. For example, scanning may begin with the 100th scan line in from the edge, while still keeping the same progression of scanning from beginning scan line towards the data line split. This embodiment is advantageous when the edges of the detector may be shielded from raw radiation by a collimator, for example.

FIG. 7 depicts a flowchart for a method 700 for the scanning of a detector without a data line split to eliminate effects of saturated pixels used in accordance with an embodiment of the present invention. First, at step 710, the object to be examined may be placed in relation to the detector. Preferably, the object is placed on one side of the detector. For example, the object may be placed so a corresponding ROI of the object (as described above) covers a portion of the detector that abuts an edge of the detector.

Next, at step 720, the detector may be exposed to an x-ray flux. The x-ray flux may cause pixels in the detector to discharge stored electrical charge, as described above. Furthermore, pixels in the ROI may discharge less electrical charge, and may therefore become unsaturated pixels. However, pixels outside the ROI may discharge most, if not all, of their stored electrical charge and may therefore become saturated.

Finally, at step 730, the pixels in the detector may be scanned along their scan lines from the one edge of the detector towards the opposite edge. For example, a scan line running along the edge of the detector opposite the edge closest to the object is activated first, scanned for data, then deactivated. Then, the next scan line closer to the object is activated, scanned, then deactivated, for example. The progression may continue until all of the scan lines have been scanned and the edge of the detector closest to the object has been scanned.

Alternatively, at step 730, the scanning of the detector may begin at a scan line other than the scan line running along the edge of the detector opposite the edge closest to the object. For example, scanning may begin with a scan line closer to the object than the edge of the detector, which is advantageous when a collimator has been used to shield the detector from raw radiation along at least part of one edge. Scanning may then progress as described above.

FIG. 8 depicts a flowchart for a method 800 for the scanning of a detector without a data line split mimicking the functionality of a detector with a data line split, used in accordance with an embodiment of the present invention. First, at step 810, an object may be positioned in relation to the detector. Preferably, the object is placed substantially in the center of the detector. For example, the object may be placed so a corresponding ROI of the object (as described above) covers the center portion of the detector.

Next, at step 820, the detector may be exposed to an x-ray flux. The x-ray flux may cause pixels in the detector to discharge stored electrical charge, as described above. Furthermore, pixels in the ROI may discharge less electrical charge, and therefore become unsaturated. However, pixels outside the ROI may discharge most, if not all, of their stored electrical charge and may therefore become saturated.

Finally, at step 830, the pixels in the detector may be scanned along their scan lines alternating from two opposite edges of the detector towards the center of the detector. For example, the scan line along one detector edge is activated, scanned and deactivated first. Next, the scan line along the opposite detector edge is activated, scanned and deactivated, for example. The scanning procedure may continue until the center of the detector has been scanned.

Alternatively, at step 830 the scanning of the detector may begin at scan lines other than the scan lines running along the edges of the detector adjacent to the edge closest to the object. For example, scanning begins with scan lines closer to the object than the adjacent edges of the detector. Scanning may then progress as described above, for example.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A method for collecting x-ray exposure data in an x-ray detector including:
providing an x-ray detector including a plurality of pixels grouped into a plurality of data lines each extending from opposite detector edges to a data line split;
placing an anatomy to be examined between said detector and said x-ray source so that a region of interest of said anatomy includes at least a portion of said data line split;
exposing said x-ray detector and said anatomy to an x-ray flux, wherein one or more of said data lines includes unsaturated pixels and saturated pixels, said saturated pixels having a larger amount of electric charge depleted than said unsaturated pixels, said unsaturated pixels located within said region of interest and said saturated pixels located outside of said region of interest;

scanning said plurality of pixels by activating said pixels in each of said data lines in a progression from each of said opposite detector edges towards said data line split; and measuring an amount of electric charge depleted in said unsaturated and said saturated pixels, wherein said scanning causes said saturated pixels to be scanned before said unsaturated pixels in one or more of said data lines.

2. The method of claim 1, wherein said providing step includes providing said data line split midway between said opposite edges.

3. The method of claim 1, wherein said scanning step includes scanning said plurality of pixels by progressing sequentially in said data lines from pixels at said opposite edges towards said data line split.

4. A method for collecting x-ray exposure data in an x-ray detector including:

providing an x-ray detector including a plurality of pixels grouped into a plurality of data lines each extending continuously from a first detector edge to an opposite detector edge, and including a plurality of scan lines perpendicular to said data lines and extending from a second detector edge to a third detector edge, said scan lines each including a plurality of said pixels, said second and third detector edges perpendicular to said first and opposite detector edges;

placing an anatomy to be examined between said detector and said x-ray source so that a region of interest of said anatomy includes at least one of said plurality of pixels;

exposing said x-ray detector and said anatomy to an x-ray flux, wherein one or more of said data lines includes unsaturated pixels and saturated pixels, said saturated pixels having a larger amount of electric charge depleted than said unsaturated pixels, said unsaturated pixels located within said region of interest and said unsaturated pixels located outside of said region of interest; and scanning said plurality of pixels by activating said pixels in each of said data lines in an alternating progression, said alternating progression including scanning each pixel in a scan line of said plurality of scan lines at said first edge, followed by each pixel in a scan line of said plurality of scan lines at said opposite edge, followed by each pixel in a scan line of said plurality of scan lines adjacent to said scan line at said first edge, followed by each pixel in a scan line of said plurality of scan lines adjacent to said scan line at said opposite edge, wherein said scanning in said alternating progression continues to scan said pixels in a scan line of said plurality of scan lines that is adjacent to previously scanned pixels until all pixels in said plurality of pixels have been scanned and causes said saturated pixels to be scanned before said unsaturated pixels in one or more of said data lines.

5. The method of claim 4, wherein said scanning step includes scanning said plurality of pixels by progressing sequentially from a pixel in each of said data lines at said first edge towards a pixel in each of said data lines at said opposite edge.

6. The method of claim 4, wherein said alternating progression of said scanning step terminates midway between said first and opposite edges.

7. The method of claim 6, further including:

providing an x-ray source of said x-ray flux; and placing an anatomy to be examined between said detector and said x-ray source, said anatomy centered between said first and opposite edges.

8. The method of claim 7, wherein said placing step causes said region of interest of said anatomy to be located in an area of said detector, said area centered between said first and opposite edges.

* * * * *